US012577516B2

(12) United States Patent
Niederbacher

(10) Patent No.: US 12,577,516 B2
(45) Date of Patent: Mar. 17, 2026

(54) PLUG FLOW FERMENTER FOR A BIOGAS PLANT

(71) Applicant: Michael Niederbacher, Bruneck (IT)

(72) Inventor: Michael Niederbacher, Bruneck (IT)

( * ) Notice: Subject to any disclaimer, the term of this patent is extended or adjusted under 35 U.S.C. 154(b) by 804 days.

(21) Appl. No.: 17/594,414

(22) PCT Filed: Mar. 20, 2020

(86) PCT No.: PCT/EP2020/057757
§ 371 (c)(1),
(2) Date: Oct. 15, 2021

(87) PCT Pub. No.: WO2020/212073
PCT Pub. Date: Oct. 22, 2020

(65) Prior Publication Data
US 2022/0213419 A1 Jul. 7, 2022

(30) Foreign Application Priority Data

Apr. 16, 2019 (DE) .......................... 102019109999.4

(51) Int. Cl.
*C12M 1/107* (2006.01)
*C12M 1/00* (2006.01)
*C12M 1/06* (2006.01)

(52) U.S. Cl.
CPC ............ *C12M 21/04* (2013.01); *C12M 27/02* (2013.01); *C12M 29/02* (2013.01)

(58) Field of Classification Search
CPC ...... C12M 21/04; C12M 27/02; C12M 29/02; C12M 27/18; C12M 23/58; C12M 43/04; C12M 45/02; C12M 47/10; B01F 27/2311; B01F 27/2312; B01F 27/251; B01F 27/60; B01F 31/00
See application file for complete search history.

(56) References Cited

U.S. PATENT DOCUMENTS

2008/0248519 A1* 10/2008 Friedmann ............ B01F 27/191
435/41
2017/0349874 A1* 12/2017 Jaques .................. B01F 27/191

FOREIGN PATENT DOCUMENTS

WO WO-2013131627 A1 * 9/2013 ........ B01F 15/00922

OTHER PUBLICATIONS

WO 2013/131627 Google Patents machine translation Sep. 3, 2024 (Year: 2024).*

* cited by examiner

*Primary Examiner* — Dean Kwak
(74) *Attorney, Agent, or Firm* — Fox Rothschild LLP

(57) ABSTRACT

The invention relates to a plug flow fermenter (1) for a biogas plant, having a reactor container (2) designed as an elongated straight tube, in the reactor interior (9) of which a substrate to be fermented, preferably by dry fermentation, can be fermented as plug flow while producing biogas, wherein the reactor container (2) has at least one container inlet (10), via which the substrate to be fermented can be fed to the reactor interior (9), and at least one container outlet (12) spaced apart from the container inlet (10) in the flow direction (x) of the plug flow, via which the fermented substrate can be discharged from the reactor interior (9), and wherein a plurality of separately exchangeable agitating devices (19) is arranged spaced apart in the reactor interior (9) when seen in the longitudinal extension direction and thus in the flow direction of the plug flow.

23 Claims, 5 Drawing Sheets

PLUG FLOW FERMENTER FOR A BIOGAS PLANT

Figure 1:
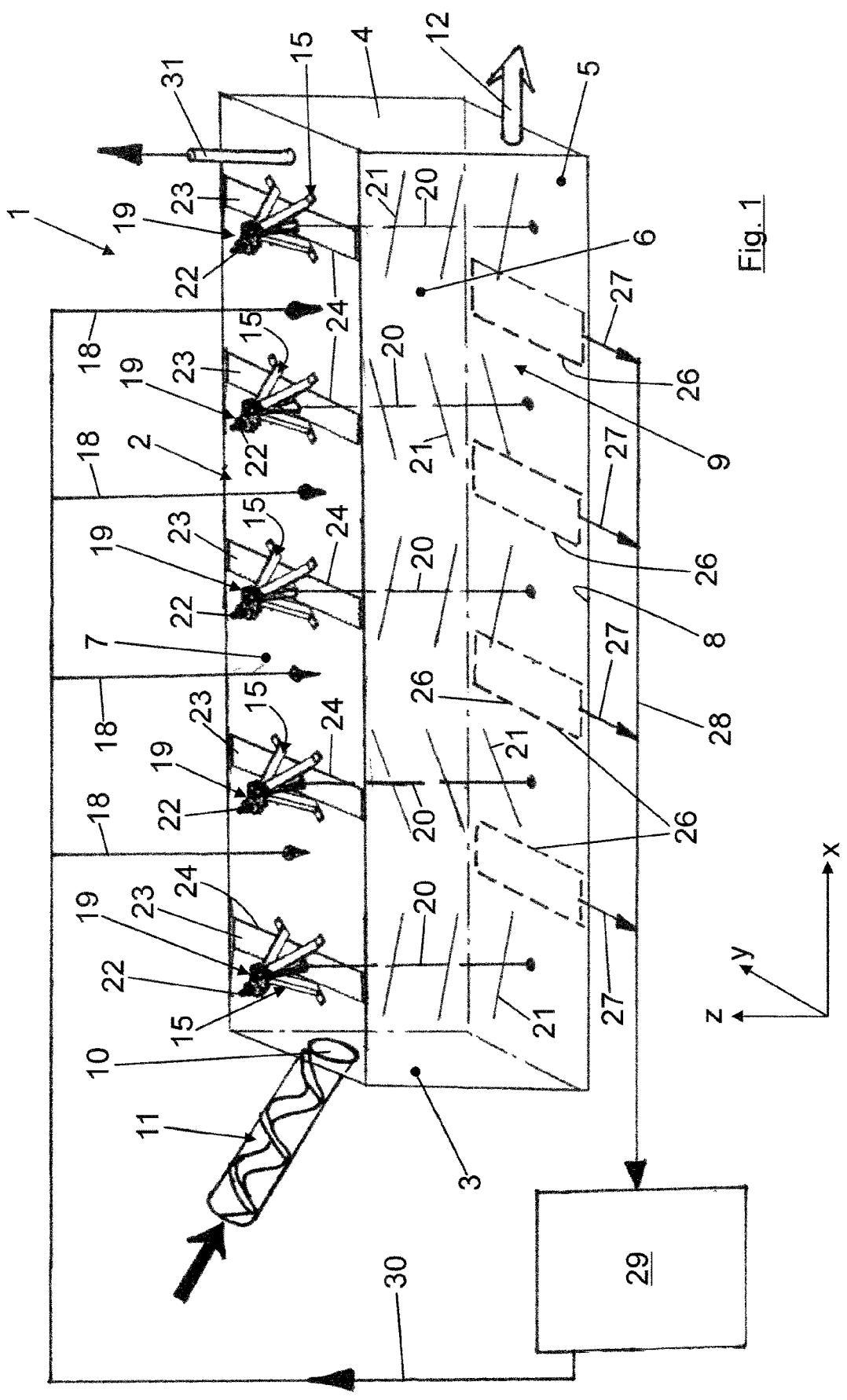

The invention relates to a plug flow fermenter for a biogas plant, a biogas plant, and a method for producing biogas.

There are basically two methods used in practice for producing biogas, namely wet fermentation and dry fermentation. The fundamental difference between wet fermentation and dry fermentation is that the dry matter content in the region of the fermenter inlet in wet fermentation is regularly between 9 and 14%, while that of dry fermentation is higher and usually >25%. The process temperatures for wet fermentation are usually around 37° C. (mesophilic), while they are usually around 55° C. (thermophilic) for dry fermentation.

The advantage of dry fermentation is that comparatively dry, fibrous and contaminated biomass, such as biowaste, organic fractions from residual waste, manure and green waste, which are problematic to process in wet-fermenting biogas plants, can be processed to produce biogas. In dry fermentation, substrates that do not compete with food production can be used to produce biogas.

There are different process variants for dry fermentation, wherein a basic distinction is made between the discontinuous or batch-wise processes and the continuous processes. In the discontinuous process, a fermentation container (a so-called garage fermenter) is filled with the substrate to be fermented, which is then fermented until the end of the predetermined retention time. In this case, a mechanical, hydraulic or pneumatic mixing of the fermenter content is omitted. The temperature control and inoculation with methane bacteria takes place via the recirculation of the percolate that accumulates in the course of the process. As soon as the dry fermentation process is completed, the fermenter containers are ventilated, wherein the resulting air-methane mixture is extracted and cleaned via a biofilter. In such a discontinuous dry fermentation process, the substrate is thus only added at the beginning of the fermentation process and the material introduced is then completely fermented. Such biogas plants are regularly constructed in a modular manner and have a plurality of fermenter containers in order to achieve a more or less uniform gas production.

In contrast to the discontinuous processes, in the continuous dry fermentation processes, similar to the wet fermentation process, the substrate is introduced continuously or at intervals into the reactor or fermenter container. For the continuous processing of substrates in the context of dry fermentation, so-called plug flow fermenters are used, in which the substrate is conveyed through the fermenter as a plug, preferably in conjunction with the use of hydraulic piston pumps. Such a plug flow fermenter is known from DE 44 16 521 A1. In this case, the fermenter is specifically designed as a horizontal cylindrical fermenter with a reactor container designed as an elongated straight tube. An axis of rotation of an agitator is mounted in the middle of the two opposite end walls of the reactor container. On this axis of rotation, agitator arms are arranged at regular, axial intervals. A similar structure is also known from EP 3 450 536 A1.

These known dry fermenters have the disadvantage that, with regular maintenance work on the agitator, the entire fermenter operation must always be stopped and the fermenter must be emptied in order to be able to service the agitator or to be able to remove and replace the agitator. This is also the case if only individual agitator paddles are damaged. The maintenance effort for such fermenters is therefore considerable and thus uneconomical and expensive.

In contrast, the problem addressed by the present invention is that of providing a plug flow fermenter for a biogas plant, comprising a reactor container designed as an elongated straight tube, by means of which the maintenance and repair of agitating devices can be carried out in a technically simple manner and without disruptive and expensive operational interruptions. The problem addressed by the present invention is also that of providing a biogas plant having such a plug flow fermenter. Lastly, the problem addressed by the present invention is also that of providing a method for producing biogas with such a plug flow fermenter.

This problem is solved by the features of the independent claims. Advantageous embodiments are the subject matter of the dependent claims back-referenced thereto.

According to claim 1, a plug flow fermenter for a biogas plant is provided, which has a reactor container designed as an elongated straight tube, in the reactor interior of which a substrate to be fermented, preferably by dry fermentation, can be fermented as plug flow while producing biogas, wherein the reactor container has a container inlet, via which the substrate to be fermented can be fed to the reactor interior, and a container outlet spaced apart from the container inlet in the flow direction of the plug flow, via which the fermented substrate can be discharged from the reactor interior. Furthermore, a plurality of separate agitating devices is arranged spaced apart in the reactor interior when seen in the longitudinal extension direction and thus in the flow direction of the plug flow, by means of which the substrate can be locally circulated and/or by means of which the substrate can be conveyed in the flow direction of the plug flow. According to the invention, the agitating devices or at least one of the agitating devices is designed as an exchangeable agitating device which, in particular also when the reactor container is filled and/or when the plug flow fermenter is in operation, can be removed from the reactor interior and/or inserted into the reactor interior, preferably removed from the reactor interior and/or inserted into the reactor interior from above when seen in the vertical axis direction.

This means that the entire fermenter operation no longer has to be stopped during maintenance work on the "agitator" (formed by the plurality of separate agitating devices) and the reactor container does not have to be emptied first in order to carry out maintenance work on the agitating devices. By dividing the agitating work between a plurality of independent or separate agitating devices, they can preferably be serviced or replaced individually without impeding the agitating work of the other agitating devices, so that the fermentation operation can be maintained. The separate agitating devices can thus be easily removed or inserted individually during ongoing operation, as a result of which biogas plants with plug flow fermenters according to the invention can be operated highly efficiently and economically.

As already mentioned above, the reactor container is designed as an elongated straight and horizontal tube, i.e., advantageously and particularly preferably designed as a completely straight tube that thus runs in a straight direction and is not curved. In this case, the term tube means in particular that the reactor container is designed to be hollow on the inside in order to form the reactor interior and can be formed, for example, by a round cylinder made of steel, for example.

However, particularly preferred is a specific design of the reactor container that can be produced easily, for example, from concrete, as a cuboid that is delimited by six rectangles forming the reactor container walls and thus has six side surfaces at right angles to one another, wherein the end walls opposite in the longitudinal extension direction or linear direction are parallel in a similar manner as the sidewalls opposite one another in the transverse direction and the bottom and top wall opposite one another in the vertical axis direction.

With the structure according to the invention, in which a plurality of exchangeable agitating devices are arranged spaced apart in the reactor interior when seen in the flow direction of the plug flow, a desired plug flow can also be realized in a functionally reliable manner and without great effort.

In principle, a plurality of agitating devices can also be arranged side by side in the transverse direction, in particular in the case of very wide or large plug flow fermenters.

According to a preferred embodiment, the agitating devices can, at least to some extent, be designed to be essentially identical and thus form identical parts, which is also advantageous in particular with regard to maintenance and installation.

Furthermore, the agitating devices can in principle have a different spacing from one another in the flow direction of the plug flow. However, one embodiment in which the agitating devices are evenly spaced apart from one another is particularly preferred. Such a uniform spacing makes it possible to achieve a plug flow in a particularly functionally reliable manner.

The agitating devices are particularly preferably aligned approximately vertically in relation to the reactor container lying in a horizontal plane, even though, in principle, an arrangement inclined to the vertical, i.e., an obliquely inclined or angled arrangement, is naturally also possible. However, the approximately vertical alignment of the agitating devices in relation to the reactor container lying in the horizontal plane allows for a particularly simple installation and arrangement of the agitating devices, in particular with a further particularly preferred embodiment, according to which the reactor container has an upper top wall when seen in the vertical axis direction, which is preferably accessible and/or preferably designed to be at least partially flat.

According to a particularly advantageous embodiment, the reactor container, preferably the top wall of the reactor container, can have an installation opening through which at least a portion of the agitating device can be introduced into the reactor interior and/or removed from the reactor interior. The installation opening ensures that the agitating device can be easily removed and inserted in a defined predetermined manner. The installation opening thus serves as a service opening through which the agitating device can be introduced into the reactor interior in a simple and functionally reliable manner from outside the reactor container and can also be removed again therefrom. In this context, it can then preferably be provided that the exchangeable agitating device extends through the installation opening with a portion received in the installed state in the reactor interior in an essentially gas-tight manner and protrudes with a portion located outside the reactor container in the installed state. As a result, this also provides easy access from the outside.

Particularly in the case of relatively large installation openings that are not completely filled and thus essentially sealed by the inserted agitating device, for example, an agitator shaft of an agitating device, the installation opening can also be closable in an essentially gas-tight manner using a cover with a single piece or multipiece design and/or designed to be removable and preferably made of stainless steel. In this case, the cover can be formed by a separate component. However, one embodiment is particularly preferred in which the cover is part of the agitating device and closes the respectively associated installation opening when the agitating device is in the inserted and installed state. Furthermore, it can alternatively or additionally be provided that the exchangeable agitating device extends through the cover with a portion received in the installed state in the reactor interior in an essentially gas-tight manner and protrudes with a portion located outside the reactor container in the installed state.

The at least one exchangeable agitating device preferably also has an agitator shaft having at least one agitator blade, which is guided from outside the reactor container through the installation opening into the reactor interior, wherein it is preferably provided that the installation opening is dimensioned such that the agitator shaft, preferably together with the at least one agitator blade arranged on the agitator shaft, can be inserted through said installation opening into the reactor interior and/or can be removed from the reactor interior through said installation opening. The installation opening thus serves specifically as a service opening through which the agitator shaft, together with the agitator blades arranged thereon, can be introduced into the reactor interior in a simple and reliable manner, for example, from the top wall, and also be removed again therefrom.

For a particularly advantageous gas-tight structure, the agitator shaft extends through the cover in an essentially gas-tight manner.

According to a further advantageous embodiment, it is proposed that the agitator shaft is assigned a preferably raised and/or funnel-shaped bearing seat, preferably made of steel, in particular stainless steel, on the bottom side in the reactor container, by means of which the free agitator shaft end is rotatably connected in the installed state or in which the free agitator shaft end is rotatably received. The connection is preferably designed as a plug-in rotary connection. A simple and precisely positioned support and mounting of each agitator shaft in the reactor container is thus achieved.

According to a particularly advantageous embodiment, it is additionally proposed that the agitator shaft can be driven by an actuating device, for example, a drive motor, which is arranged outside the reactor container and preferably supported and/or mounted on the top wall. This results in a particularly compact, function-integrated structure of an agitating device together with an advantageous support for same. An electric drive motor or a pneumatically or hydraulically operated drive motor is suitable as the drive motor.

A further particularly advantageous embodiment provides that, on the side of the installation opening facing the reactor interior, an apron is arranged, preferably made of stainless steel, which protrudes from the installation opening in the direction of the reactor interior and surrounds the installation opening in an annular manner and dips into the substrate when in the sealing position. This apron ensures that the exchangeable agitating devices, for example, an agitator shaft together with agitator blades arranged thereon, can be introduced into or removed from the reactor interior essentially in a gas-tight manner or without an unnecessarily large loss of gas. This apron can in principle be integral with the reactor container, but is preferably formed by a separate component and, for example, immobilized from below on the opening edge region around the installation opening.

However, alternatively, the apron can also be hooked into the installation opening from above and supported or mounted on the opening edge region around the installation opening. For immobilizing the apron, it has, for example, a flange region which then bears against the opening edge region either from below or from above. The apron is also preferably immobilized via releasable screw connections, so that the apron can also be exchanged if necessary and replaced with a new apron. In the case of the presence of a flange region, the apron is then releasably immobilized via said flange region on the opening edge region by means of the screw connection.

According to a further particularly preferred embodiment, the installation opening is designed to be slot-like and extends in the region between two transversely opposite reactor container wall regions, preferably reactor container sidewalls, which, for example, is particularly advantageous in connection with agitator blades extending away from the agitator shaft on opposite sides because in this case, the agitator shaft together with the agitator blades can then be easily introduced and removed possibly without folding the agitator blades up or down.

The installation openings and/or the covers are preferably designed to be essentially identical and/or, when seen in the longitudinal extension direction of the reactor container, lie spaced apart and one behind the other in a straight line or in straight alignment and/or are aligned parallel to one another.

According to a particularly preferred specific embodiment, it is provided that the agitating devices each have a plurality of agitator blades extending away from the agitator shaft on opposite sides and lie in a vertical plane. With such a structure, a particularly simple introduction and removal of the agitator shaft together with the agitator blades is possible without folding the agitator blades up or down. This is preferably achieved such that, on a first side of the agitator shaft, a plurality of agitator blades, one above the other and spaced apart from one another when seen in the vertical axis direction, protrudes from the agitator shaft, and that, on an opposite side of the agitator shaft spaced apart by 180°, a plurality of agitator blades, one above the other and spaced apart from one another when seen in the vertical axis direction, also protrudes from the agitator shaft, wherein it is preferably provided that the agitator blades on the second side are offset in the vertical axis direction with respect to the agitator blades on the first side.

According to a further particularly preferred embodiment according to the invention, a bottom-side collecting channel, in particular a sand collecting channel, is assigned to at least some of the agitating devices. In this case, the term "assigned" is to be interpreted in a broad sense and means that such a collecting channel can in principle be located essentially on the bottom side below the respective agitating devices or agitator shaft. However, this term is also supposed to comprise designs in which the collecting channel is arranged, for example, in the middle between two agitating devices spaced apart in the flow direction of the plug flow. In connection with the bottom-side collecting channels, it is only essential that material to be removed from the reactor interior, in particular a substrate-sand mixture as material to be removed, collects therein, in particular when an "assigned" agitating device is actuated. The term removal channel is also to be understood in a broad sense and is also intended to comprise large-scale removal devices, for example, a removal shaft as a removal channel. Furthermore, in connection with this embodiment, a removal device is provided, by means of which the material accumulating in the collecting channel can be removed from the at least one collecting channel. Such a design ensures that the material settling in the reactor interior and to be removed collects in a defined manner in the collecting channels, from where it can be removed in a functionally reliable manner.

Furthermore, a separator can be provided to which the material removed by means of the removal device is fed and in which the removed material, preferably the aforementioned substrate-sand mixture, can be separated into a substrate phase and a waste phase, in particular a sand phase. Particularly preferred in this context is a design in which a return device is also provided, by means of which the substrate phase separated in the separator can be fed to the reactor interior as percolate, i.e., preferably fed as percolate to the substrate from above when seen in the vertical axis direction. Such a return device is expressly only provided as an option, i.e., in principle, only a separator can be provided, so that the percolate must then be fed to the substrate in the reactor interior in a different way, for example, to achieve an inoculation of the substrate. Herein, the term separator is expressly to be interpreted broadly and is also expressly intended to comprise designs such as a settling basin.

Furthermore, the removal device preferably has a removal line guided to each collecting channel, wherein the removal lines open into a collecting line which is guided to the separator. One component of the removal device is also at least one conveying device, for example, a removal pump, by means of which the material to be separated can be removed from the collecting channels and conveyed into the separator. In addition, locking elements, for example, valves, can be provided, by means of which the removal is controlled at specific times. Analogous hereto, the return device can be designed having a return line, at least one conveying device, such as a pump, and a locking element, such as a valve, in order to control the return in a functionally reliable manner at specific times.

Particularly alternatively, but possibly also additionally to a collecting channel or collecting shaft solution as described above, it can also be provided that a plurality of removal lines, spaced apart in the longitudinal extension direction, is provided on the reactor container, said removal lines forming a removal device and being guided, preferably through a lateral or outer wall of the reactor container, into the bottom-side, lower region of the reactor interior, so that a material to be removed, in particular a substrate-sand mixture, can be removed from the reactor container via said removal device. In this case, it can also be provided, for example, that the removal lines open into a collecting line. Such an arrangement may help to avoid removal channels and removal shafts. Analogous to the solution described above in connection with the collecting channels or collecting shafts, the removed material can in this case also be fed, either directly from the individual removal lines or indirectly via a collecting line connecting the removal lines, to a separator or settling basin in which the removed material, preferably the aforementioned substrate-sand mixture, can be separated into a substrate phase and a waste phase, in particular a sand phase.

The at least one container inlet and the at least one container outlet are preferably arranged in the flow direction on opposite end regions of the reactor container, preferably on end walls spaced apart from one another and aligned parallel to one another in the longitudinal extension direction of the reactor container.

The reactor container can basically have any cross-sectional shape. However, one particularly preferred embodiment provides that the walls of the reactor container, when seen in cross section through the reactor container, form a frame surrounding the reactor interior. In this case, the walls of the reactor container preferably form a rectangular reactor interior in relation to the cross section through the reactor container. Such a reactor container is easy to manufacture, for example, from concrete or stainless steel.

Preferably, the plug flow fermenter according to the invention further has at least one gas extraction device, by means of which the biogas formed in the reactor interior can be extracted from the reactor container. In this case, it is particularly preferred that at least one gas extraction line of the gas extraction device is guided into the reactor interior in the region of the container outlet. This ensures that the biogas is discharged in a functionally reliable manner precisely in the region in which the fermentation process and thus the production of biogas are essentially completed. Once again, it goes without saying that the gas extraction device can naturally have an extraction line that is coupled to a conveying device, such as a pump, wherein controllable valves can once again be provided as locking elements, by means of which the biogas extraction is controlled according to the respective requirements.

Furthermore, a feed device, for example, a feed screw, is preferably provided, by means of which the substrate to be fermented can be fed to the reactor interior via the at least one container inlet in a functionally reliable manner.

Furthermore, the plug flow fermenter according to the invention can have a discharge device for a functionally reliable discharge of the fermented substrate from the reactor interior, by means of which the fermented substrate can be discharged via the container outlet. For example, such a discharge device can be formed by a discharge pump as a conveying device.

The plug flow fermenter further preferably has a control device, by means of which the feed into and the discharge from the reactor container and thus the retention time of the substrate in the reactor container are controllable in an open-loop or closed-loop manner. The open-loop control or closed-loop control is preferably carried out such that the retention time in the reactor container is between 25 and 50 days. Such a retention time has proven to be particularly advantageous in order to achieve an effective biogas production with a high biogas yield in connection with a plug flow fermenter according to the invention.

The substrate to be fermented, preferably by dry fermentation, particularly preferably has a dry matter content in the reactor container of 12 to 40% DM, preferably 19 to 30% DM.

The advantages that can be achieved with the biogas plant according to the invention or with the process control according to the invention correspond to those of the plug flow fermenter. In this respect, reference is made to the previous statements in order to avoid repetitions.

Figure 2:
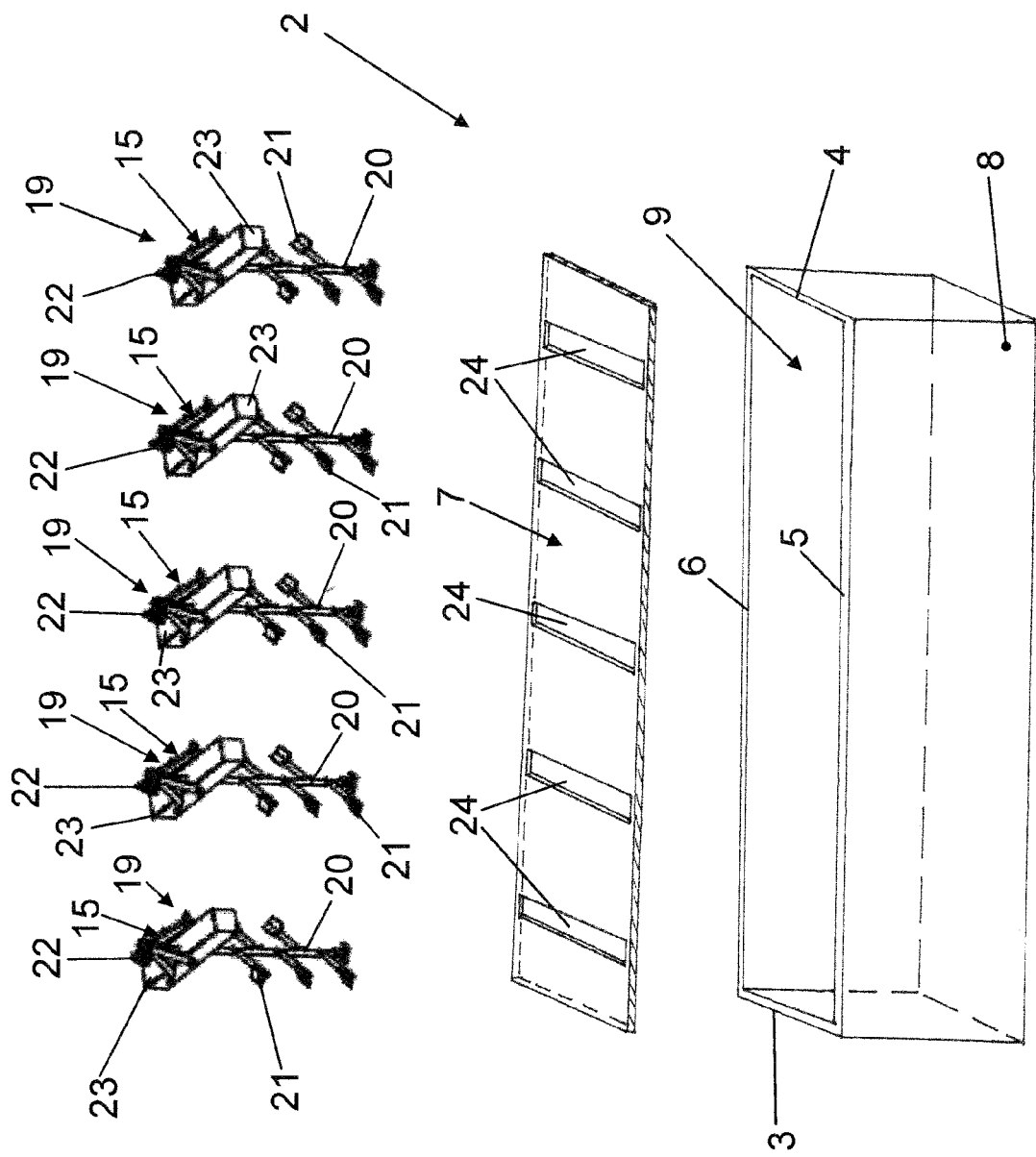
Figure 3:
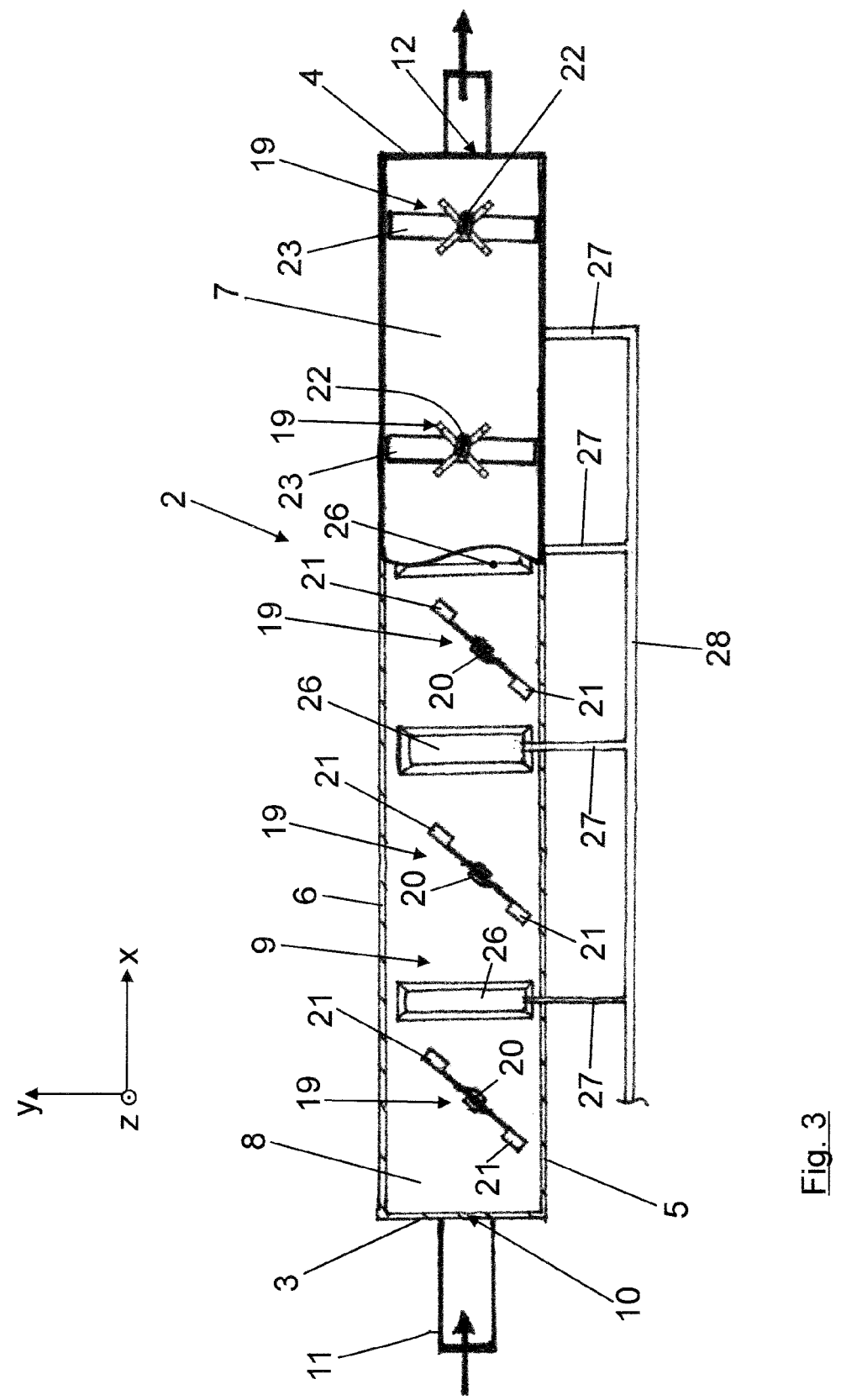
Figure 4:
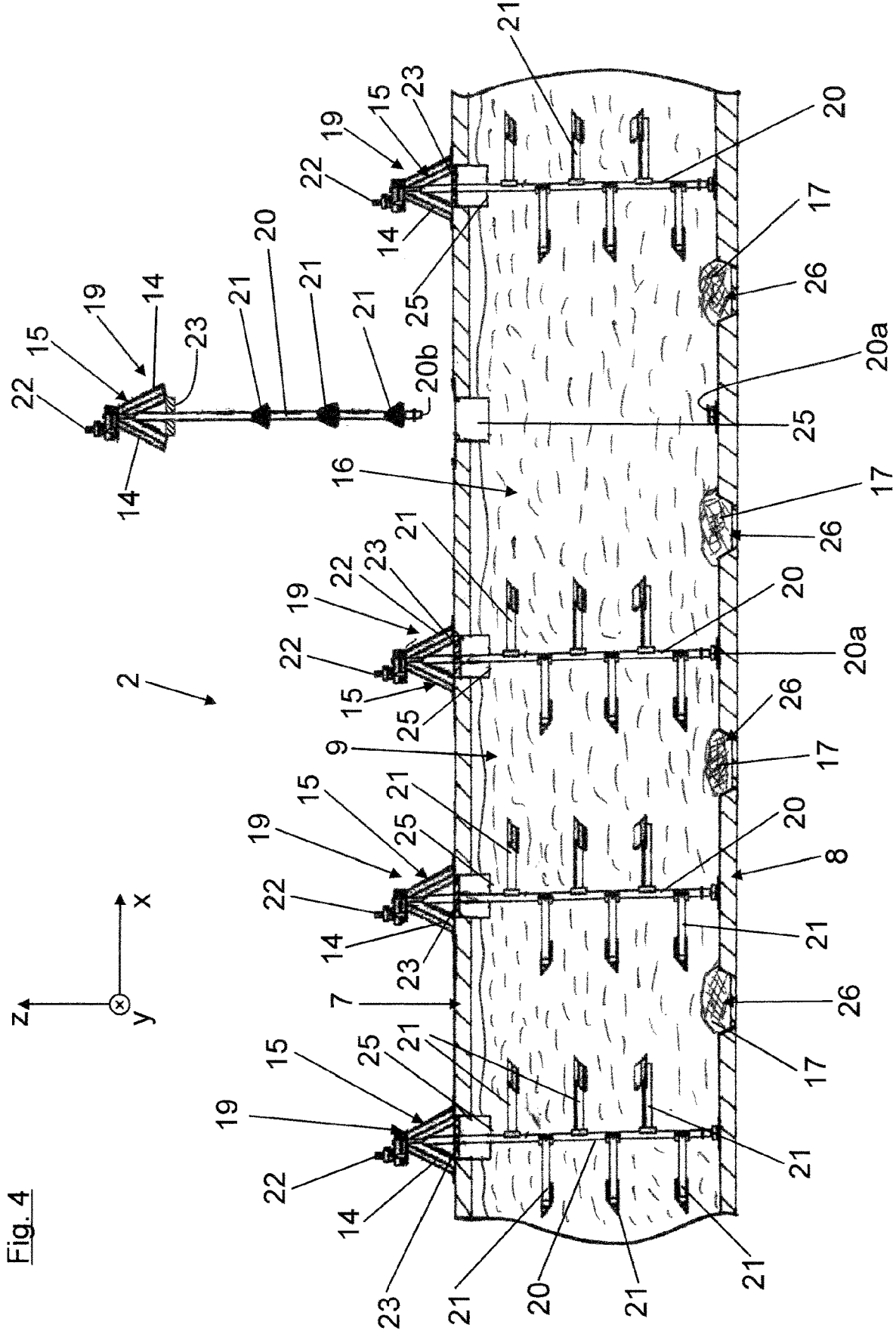
Figure 5:
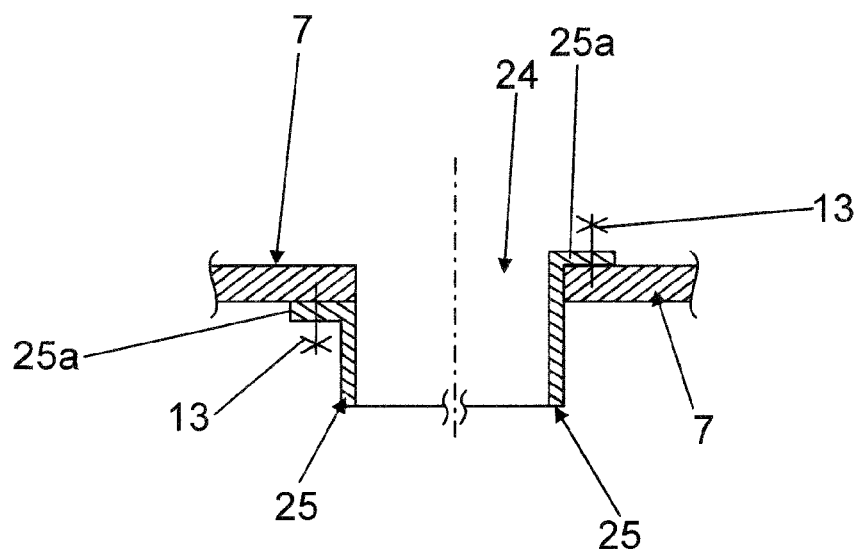

In the following, the invention will be described in more detail using drawings, in which:

FIG. 1 schematically shows a perspective depiction of an exemplary embodiment of a plug flow fermenter according to the invention;

FIG. 2 is a schematic, perspective exploded view with regard to the essential components of FIG. 1;

FIG. 3 schematically shows a top view of the fermenter according to FIG. 1 with a partially omitted top wall;

FIG. 4 is a schematic side view of a portion of the exemplary fermenter according to the invention according to FIG. 1 with the sidewall omitted; and FIG. 5 schematically shows a basic sketch with two alternative fastening options for the apron, wherein the left half of the drawing shows a first embodiment and the right half of the drawing shows an alternative, second embodiment.

FIG. 1 schematically shows a perspective depiction of an exemplary embodiment of a plug flow fermenter 1 according to the invention, which is, for example, part of a biogas plant not shown in detail. As can be seen in particular from FIG. 2, which is a schematic exploded view of the essential components of the plug flow fermenter 1 of FIG. 1, and from FIG. 3, the plug flow fermenter 1 has a reactor container 2 designed as an elongated straight tube. In this case, this reactor container 2 is designed in the form of a container or cuboid merely by way of example and has a first or front end wall 3 and a second or rear end wall 4 located opposite in the longitudinal extension direction x of the reactor container and thus in the flow direction of the plug flow. The reactor container 2 also has two sidewalls 5 and 6 opposite one another in the transverse direction y and a bottom wall 8.

As can be seen from FIGS. 1 to 4, the reactor container 2 also has an upper, preferably accessible and flat, top wall 7 that is opposite the bottom wall 8 in the vertical axis direction z. In this case, the reactor container 2 is thus designed, by way of example, as an elongated straight-line cuboid that is delimited by six rectangles forming the reactor container walls 3, 4, 5, 6, 7, and 8 and thus has six side surfaces that are at right angles to one another, wherein the end walls 3, 4 opposite one another in the longitudinal extension direction x or linear direction are as parallel as the sidewalls 5, 6 opposite one another in the transverse direction y and the top wall 7 and the bottom wall 8 opposite one another in the vertical axis direction z. The walls 5, 6, 7, and 8 of the reactor container 2 also form a rectangular reactor interior 9 based on the cross section (sectional plane y-z) through the reactor container 2, but this is only to be understood as an example. The reactor container can naturally also have other internal and also other external geometries, for example, be designed to be at least partially rounded at the internal and/or external corners in order to form, for example, a more circular or oval cross section. Semicircular cross sections are also conceivable, to name just one further example.

Herein, the reactor container 2 is shown in a horizontal position which also corresponds to its most common use and which is why such fermenters are also called horizontal fermenters. The walls of the fermenter can be made of any suitable material, for example, concrete or stainless steel.

By way of example, the reactor container 2 herein has a container inlet 10 in the region of the first end wall 3, via which a substrate to be fermented can be fed continuously or at specific times in an interval-like manner by means of a feed device which in this case is designed as a feed screw 11 by way of example. By pressing in the substrate, a feed force for the plug flow is generated preferably simultaneously in its flow direction, which corresponds to the longitudinal extension direction x of the reactor container 2.

Furthermore, a container outlet 12 is provided on the opposite second end wall 3 of the reactor container 2, via which the fermented substrate can be discharged from the reactor interior 9 by means of a discharge device designed, for example, as a discharge pump.

Furthermore, a plurality of agitating devices 19 spaced apart when seen in the flow direction x of the plug flow is arranged in the reactor interior 9, by means of which the substrate to be fermented can be locally circulated and/or by means of which the substrate can be conveyed in the flow direction x of the plug flow.

The agitating devices 19 are preferably designed to be essentially identical and, in addition, are preferably evenly spaced apart from one another.

The agitating devices 19 are also aligned vertically with respect to the horizontal reactor container 2, i.e., in the vertical axis direction z, and in this case, each have, for example, an agitator shaft 20 guided from outside the reactor container 2 through the top wall 7 with a plurality of agitator blades 21 spaced apart from one another in the longitudinal direction of the agitator shaft.

In this case, the agitating device 19 specifically has, for example, a plurality of agitator blades 21 extending away from the agitator shaft 20 on opposite sides and lying in a vertical plane (see in particular FIGS. 2 and 4), wherein, on a first side of the agitator shaft 20, a plurality of agitator blades 21, one above the other and spaced apart from one another when seen in the vertical axis direction, protrudes from the agitator shaft 20, and wherein, on an opposite side of the agitator shaft 20 spaced apart by 180°, a plurality of agitator blades 21, one above the other and spaced apart from one another when seen in the vertical axis direction, also protrudes from the agitator shaft 20. As can also be seen here, the agitator blades 21 on the second side are offset by way of example in the vertical axis direction z with respect to the agitator blades 21 on the first side.

As can also be seen in particular from the figures, the agitating devices 19 also each have an actuating device, for example, a drive motor 22, which is arranged outside the reactor container 2 and supported and mounted on the top wall 7 by means of a support device 15. The agitator shaft 20 can be rotationally driven by means of the drive motor 22. In this case, the support device 15 is formed by way of example by a frame carrying the drive motor 22 with a plurality of support legs 14 which are arranged around the agitator shaft 20 and fan out towards the bottom.

As can be seen in particular from FIG. 1 in conjunction with FIGS. 2, 3, and 4, the top wall 7 has an installation opening 24 in the region of the agitator shaft lead-through, which can be closed in a gas-tight manner by means of a cover 23 preferably made of stainless steel, wherein the agitator shaft 20 extends through the cover 23 in a gas-tight manner. The installation openings 24 are also dimensioned such that the agitator shaft 20, together with the agitator blades 21, can be introduced into and removed from the reactor interior 9 through said installation openings. For this reason, the installation openings 24 extend in this case, by way of example, in a slot-like manner essentially over the entire width of the top wall 7, i.e., in the transverse direction y between the sidewalls 5 and 6. In addition, the installation openings 24 also lie spaced apart and one behind the other in a straight line or in straight alignment when seen in the longitudinal extension direction x, and are preferably all designed to be identical and/or aligned parallel to one another. In this case, the same also applies to the covers 23 in their installed state.

On the side of the installation opening 24 facing the reactor interior 9, an apron 25 is arranged, preferably made of stainless steel, which protrudes from the installation opening 24 in the direction of the reactor interior 9 and surrounds the installation opening 24 in an annular manner and dips into the substrate 16 when in the sealing position (see in particular FIG. 4). This apron 25 is preferably formed by a separate component and, for example, as shown in the left half of FIG. 5, can be immobilized from below on the opening edge region around the installation opening 24. However, alternatively (the right half of FIG. 5), the apron 25 can also be hooked into the installation opening 24 from above and supported or mounted on the opening edge region around the installation opening 24. For immobilizing the apron 25, it has in both alternative embodiments preferably a flange region 25a which bears against the opening edge region (from below in the first alternative of the left half of the drawing and from above in the second alternative of the right half of the drawing). In this case, by way of example and specifically, the apron 25 is immobilized via its flange region 25a in each case preferably via releasable screw connections 13, so that the apron can also be exchanged if necessary and replaced with a new apron.

As is shown in FIG. 1 only by way of example and schematically and with dashed lines, at least some of the agitating devices 19 are assigned a bottom-side collecting channel 26 in which, in particular when the agitating devices 19 are actuated, material 17 (see FIG. 4), in particular a substrate-sand mixture, to be removed from the reactor interior 9 accumulates. The collecting channels 26 are each arranged spaced apart between two agitating devices 19 merely by way of example, wherein the collecting channels 26 in this case extend further, for example, in the transverse direction y between the sidewalls 5 and 6. The collecting channels 26 can be designed, for example, as trough-shaped depressions, into each of which a removal line 27 opens, which in turn is part of a removal device, by means of which the material 17 accumulating in the respective collecting channel 26 can be removed from the collecting channel 26.

In this case, the removal lines 27 open, for example, into a collecting line 28, via which the removed material is fed to a separator 29 of the removal device, in which the removed material, preferably a substrate-sand mixture, is separated into a substrate phase and a waste phase, preferably a sand phase.

A return line 30 of a return device then leads from the separator 29 back to the reactor container 2, so that the substrate phase separated in the separator 29 can be fed to the reactor interior as percolate, preferably fed as percolate to the substrate from above when seen in the vertical axis direction z. This is shown in FIG. 1 merely by way of example and schematically by means of a plurality of percolate lines 18 branching off from the return line 30. It goes without saying that only a single percolate line or a different number of percolate lines can also be provided.

Alternatively to this above-described solution with the collecting channels, it can also be provided that possibly no collecting channels 26 are provided and instead only a plurality of removal lines 27 spaced apart from one another along or around the reactor container 2 is provided. These removal lines 27 then form a removal device and in this case are guided, for example, through the sidewall 5 of the reactor container 2 into the bottom-side lower region of the reactor interior 9, so that a material 17 to be removed, in particular a substrate-sand mixture, can be removed from the reactor container 2 via said removal lines and fed to the collecting line 28. Via said collecting lines, the removed material is fed to the separator 29 analogously to the above description, in which the removed material, preferably a substrate-sand mixture, is separated into a substrate phase and a waste phase, preferably a sand phase. If necessary, the above-described solution and the solution with collecting channels can also be realized together, so that two types of removal lines 27 are thus provided, namely removal lines 27 guided to the collecting channels 26 and removal lines 27 not guided to the collecting channels 26. In the latter case, one collecting line 28 can then be provided for all of the removal lines 27 or two collecting lines 28 can be provided, i.e., one collecting line 28 for each of the different types of removal lines 27.

The dosing of the biomass, the discharge of the biomass, the actuation of the agitating devices, the removal of the material from the collecting channels 26 (if present) and the return of the substrate to the reactor container 2 are in this case all carried out in a controlled manner by means of a control device (not depicted). By means of said control device, in particular the feed into and the discharge from the reactor container 2 and thus the retention time of the substrate in the reactor container 2 are controlled in an open-loop and closed-loop manner. The open-loop or closed-loop control is preferably carried out such that the retention time in the reactor container 2 is between 25 to 50 days and/or that the substrate in the reactor container 2 has a dry matter content of 12 to 40% DM, preferably 19 to 30% DM.

Furthermore, a gas extraction device 31 is provided, by means of which the generated biogas (methane gas) can be extracted from the reactor container 2.

If an agitating device 19 or a plurality of agitating devices 19 is to be replaced while the plug flow fermenter 1 is in operation, i.e., when the reactor container 2 is full or filled, it can be achieved in a simple manner with the present invention such that the agitating device 19 designated for replacement, as shown schematically and by way of example in FIG. 4 using the second agitating device 19 from the right, is simply lifted out through the installation opening 24. For this purpose, as shown by way of example in FIG. 4, it is particularly advantageous (but not mandatory) if the substrate 16 in the reactor interior 9 has such a filling height in the vertical axis direction z that the apron 25 dips into the substrate 16, since an essentially gas-tight state is then established in the region of the installation opening 24, which allows for the cover 23 to be opened and the agitating device 19 to be lifted out or removed without any significant gas escaping from the installation opening 24 or from the reactor container 2. The same applies, of course, in an analogous manner to a reinsertion of the or a new agitating device 19.

As can also be seen from FIG. 4, the removed agitating device 19 has in this case been rotated with respect to the agitator blades 21 spaced apart by 180° such that the agitator blades 21 are aligned in the direction of the slot-shaped installation opening 24 and the agitator shaft 20 together with the agitator blades 21 can thus be introduced into, as well as removed from, the reactor interior 9 in the simplest manner.

In this case, the agitator shafts 20 are assigned on the bottom side in the reactor container 2, i.e., on the inner side of the bottom wall 8, a bearing seat 20a, preferably made of steel, in particular stainless steel, which herein is raised by way of example and optionally also widens upward into a funnel shape (not depicted), in which the free agitator shaft end 20b is rotatably received in the installed state, wherein it is preferably provided that the connection is designed as a plug-in rotary connection.

The cover 23 with a single piece or multipiece design can, as shown in the figures, be part of the agitating device 19 and, when the agitating device 19 is in the inserted, installed state, can close the associated installation opening 24, preferably close it in a gas-tight manner. Alternatively hereto, the cover 23 can in principle also be formed by a separate component that can be handled independently of the agitating device 19. In this case, the cover has then, for example, a multipiece design in order to be able to arrange it around the agitator shaft 20 in a simple and gas-tight manner.

In both above-described variants, the cover 23 can be arranged in the region of the installation opening 24, for example, resting on the edge region, such that the cover 23 can also be immobilized on the surrounding reactor container wall region by means of releasable fastening means.

What is claimed is:

1. A plug flow fermenter for a biogas plant, said plug flow fermenter comprising:
    a reactor vessel comprising a tubular body having a longitudinal axis that extends in a horizontal orientation, said tubular body defining a reactor interior configured to direct substrate along said longitudinal axis in a generally linear flow path;
    wherein said reactor vessel includes at least one inlet positioned at a first longitudinal end of said reactor vessel, and at least one outlet positioned at an opposite longitudinal end of said reactor vessel spaced apart from said at least one inlet, said at least one outlet permitting discharge of fermented substrate from said reactor interior along said longitudinal axis;
    wherein a plurality of separate agitator devices are arranged in said reactor interior, said plurality of separate agitator devices being spaced apart in linear fashion along said longitudinal axis, each agitator device comprising a shaft with at least one agitator blade mounted thereon, said shafts being oriented perpendicular to said longitudinal axis and configured to impart localized mixing of said substrate as said substrate flows along said longitudinal axis; and
    wherein at least one of said plurality of separate agitator devices is mounted within a vertically oriented installation opening formed in an upper portion of said reactor vessel, said installation opening being dimensioned such that said agitator shaft and said at least one agitator blade can be inserted through and removed through said installation opening without removal of adjacent reactor components during a fermenting operation.

2. The plug flow fermenter set forth in claim 1, wherein said plurality of separate agitator devices are uniformly spaced from one another along said longitudinal axis.

3. The plug flow fermenter set forth in claim 1, wherein said tubular body of said reactor vessel has a horizontal orientation, and said plurality of separate agitator devices are oriented in a generally vertical direction and spaced apart along said longitudinal axis of said reactor vessel.

4. The plug flow fermenter set forth in claim 1, wherein said reactor vessel includes an at least partially flat ceiling wall.

5. The plug flow fermenter set forth in claim 1, wherein said reactor vessel includes a plurality of installation openings, each installation opening configured to receive one of said agitator devices from above, including its agitator shaft and blades, and to allow removal vertically upward, and wherein each said agitator device and installation opening together form a gas-tight interface about said agitator shaft.

6. The plug flow fermenter set forth in claim 5, wherein each said agitator device includes a removable cover that forms a gas-tight seal about said installation opening.

7. The plug flow fermenter set forth in claim 6, wherein at least one said removable agitator device includes an agitator shaft extending from outside said reactor vessel through said installation opening into said reactor interior, said agitator shaft having at least one agitator blade mounted thereon;

wherein said installation opening is formed to permit said agitator shaft and said at least one agitator blade to pass therethrough during installation and removal without dismantling said agitator blade.

8. The plug flow fermenter set forth in claim 7, wherein said agitator shaft extends through said removable cover in gas-tight fashion.

9. The plug flow fermenter set forth in claim 7, wherein a bottom portion of said reactor interior includes a series of receptacles, each said receptacle configured to receive a bottom end of one of said agitator shafts in a configuration that forms a plug-in rotary connection therewith.

10. The plug flow fermenter set forth in claim 9, wherein a portion of said agitator shaft extending above said reactor vessel is connected to and driven by a drive motor selected from the group consisting of an electrically powered motor, a pneumatically powered motor and a hydraulically powered motor.

11. The plug flow fermenter set forth in claim 5, further including an apron removably positioned within said installation opening, said apron having a ring-shaped structure and protruding into said reactor interior while in a sealed position within said installation opening.

12. The plug flow fermenter set forth in claim 11, wherein said apron includes a flange that abuts said reactor vessel within said reactor interior, and is secured thereto via at least one detachable screw.

13. The plug flow fermenter set forth in claim 5, wherein each of said installation openings has an elongated slot-like geometry, and wherein each installation opening is oriented in said longitudinal direction of said reactor vessel.

14. The plug flow fermenter set forth in claim 7, wherein said agitator device includes a plurality of agitator blades extending away from said agitator shaft on opposite sides thereof in a staggered, alternating arrangement.

15. The plug flow fermenter set forth in claim 1, wherein at least one of said plurality of said agitator devices includes a bottom-side collecting channel, having an outlet opening connected to a discharge conduit for removal of accumulated substrate from said reactor interior.

16. The plug flow fermenter set forth in claim 1, further including a plurality of discharge lines spaced apart along said longitudinal axis and operatively connected to a collecting line, said discharge lines and collecting line forming a discharge device for withdrawing fermented substrate from said reactor interior.

17. The plug flow fermenter set forth in claim 16, further including a separator, wherein fermented substrate withdrawn by means of said discharge device is fed into said separator and separated into a waste phase and a substrate phase; and wherein said substrate phase is returned to said reactor interior via a return line as a percolate.

18. The plug flow fermenter set forth in claim 1, wherein said at least one inlet is located at a first longitudinal end of said reactor vessel, and said at least one outlet is located at a second, opposed longitudinal end.

19. The plug flow fermenter set forth in claim 1, wherein said reactor vessel is formed by four walls that form a cross-sectional shape of a rectangle.

20. The plug flow fermenter set forth in claim 1, further including a gas extraction device operatively attached to said reactor vessel for extracting biogas formed within said reactor interior.

21. The plug flow fermenter set forth in claim 1, further including a feed device operatively connected to said at least one inlet for feeding substrate to be fermented into said reactor interior in a horizontal flow direction along said longitudinal axis, and including a discharge device operatively connected to said at least one outlet for removing fermented substrate from said reactor interior in said horizontal flow direction.

22. The plug flow fermenter set forth in claim 21, further including a control device operatively connected to said feed device and said discharge device, said control device being configured to regulate the retention time of said substrate within said reactor vessel for a time period ranging from about 25 days to about 50 days.

23. The plug flow fermenter set forth in claim 1, wherein said substrate to be fermented has a dry matter content from about 12% to about 40% DM.

* * * * *